(12) United States Patent
Martinez-Conde et al.

(10) Patent No.: US 8,721,081 B2
(45) Date of Patent: May 13, 2014

(54) METHOD OF DETECTING NEUROLOGICAL DISEASE

(75) Inventors: Susana Martinez-Conde, Anthem, AZ (US); Stephen L. Macknik, Anthem, AZ (US); Xoana Troncoso, Pasadena, CA (US); Jorge Otero-Millan, Phoenix, AZ (US)

(73) Assignee: Dignity Health, Phoenix, AZ (US)

( * ) Notice: Subject to any disclaimer, the term of this patent is extended or adjusted under 35 U.S.C. 154(b) by 249 days.

(21) Appl. No.: 13/359,828

(22) Filed: Jan. 27, 2012

(65) Prior Publication Data

US 2012/0238903 A1   Sep. 20, 2012

Related U.S. Application Data

(63) Continuation-in-part of application No. 12/740,008, filed as application No. PCT/US2008/082034 on Oct. 31, 2008, now Pat. No. 8,348,428.

(60) Provisional application No. 61/437,138, filed on Jan. 28, 2011, provisional application No. 60/984,628, filed on Nov. 1, 2007.

(51) Int. Cl.
*A61B 3/14* (2006.01)
*A61B 3/113* (2006.01)

(52) U.S. Cl.
CPC ..................................... *A61B 3/113* (2013.01)
USPC .......................................... 351/209; 351/246

(58) Field of Classification Search
CPC ....................................................... A61B 3/113
USPC ................................. 351/205, 209, 210, 246
See application file for complete search history.

(56) References Cited

U.S. PATENT DOCUMENTS

| 8,348,428 B2 * | 1/2013 | Martinez-Conde et al. .. 351/209 |
| 2003/0028081 A1 | 2/2003 | Blazey et al. |
| 2010/0191156 A1 | 7/2010 | Sakamoto et al. |
| 2010/0277693 A1 | 11/2010 | Martinez-Conde et al. |
| 2012/0081666 A1 * | 4/2012 | Kiderman et al. ............ 351/210 |

FOREIGN PATENT DOCUMENTS

| WO | 2012/103470 A2 | 8/2012 |
| WO | 2011/103470 A3 | 11/2012 |

OTHER PUBLICATIONS

Written Opinion of the International Searching Authority for PCT/US2012/022959.

* cited by examiner

*Primary Examiner* — Huy K Mai
(74) *Attorney, Agent, or Firm* — Husch Blackwell LLP (57) ABSTRACT

A method and apparatus are provided for the differential diagnosis of a patient with progressive supranuclear palsy (PSP) from a patient with Parkinson's disease (PD). One method includes identifying a plurality of partially repetitive eye movements that over time define square wave jerks, each square wave jerk of the plurality of square wave jerks defined by a first horizontal saccadic movement that moves the eye away from a fixation target followed by a corrective saccadic movement towards the target shortly thereafter, measuring a vertical component associated with the plurality of square wave jerks, comparing the vertical component with a threshold value. PSP or PD is identified by comparison of the vertical component with the threshold value. In another embodiment, a patient's saccade rate is determined and compared to a threshold value, and PSP or PD is identified based upon the comparison of the saccade rate with the threshold value.

30 Claims, 7 Drawing Sheets

1ST SACCADE IN RED; ACCEPTABLE DIRECTIONS OF 2ND SACCADE IN BLUE

Fig. 4B

AVG. MAGNITUDE OF 1ST AND 2ND SACCADE

DIFFERENCE IN DIRECTION BETWEEN THE 1ST AND THE 2ND SACCADE (DEG.)

Fig. 4E

RELATIVE MAGNITUDE DIFFERENCE OF 1ST AND THE 2ND SACCADE (%)

Fig. 4F

INTER-SACCADIC INTERVAL (MS)

Fig. 7B

METHOD OF DETECTING NEUROLOGICAL DISEASE

CROSS REFERENCE TO RELATED APPLICATIONS

The present application claims the benefit of U.S. Provisional Patent Application Ser. No. 61/437,138 filed on Jan. 28, 2011, and is a continuation-in-part of U.S. patent application Ser. No. 12/740,008 filed on Jul. 15, 2010 (pending), which claims the benefit of PCT Pat. Application Serial No. PCT/US08/82034 filed on Oct. 31, 2008, which claims the benefit of U.S. Provisional Patent Application Ser. No. 60/984,628 filed on Nov. 1, 2007, each of which is incorporated by reference.

FIELD OF THE INVENTION

The field of the invention relates to using eye movements as a way to provide differential diagnosis of progressive supranuclear palsy from Parkinson's disease.

BACKGROUND OF THE INVENTION

The eye movements of people with neurological disease differ significantly from those of healthy people. In addition, eye movements among people with seemingly similar but different neurological diseases can also be different from each other. Because of the importance of accurate diagnosis of neurological diseases, a need exists for better methods of evaluating such differences.

The eyes do not stay perfectly still during visual fixation. Fixational eye movements and saccadic intrusions continuously change the position of the gaze.

Microsaccades are rapid, small-magnitude involuntary saccades that occur several times each second during fixation; microsaccades counteract visual fading and generate strong neural transients in the early visual system. Microsaccades may also drive perceptual flips in binocular rivalry. Microsaccade rates and directions are moreover modulated by attention, and thus generate rich spatio-temporal dynamics. Further, fixational eye movements as a whole enhance fine spatial acuity.

The most common type of saccadic intrusion is referred to as a square wave jerk (SWJ). SWJs are characterized by one small horizontal saccadic movement that moves the eye away from the fixation target, followed by a corrective saccade towards the target shortly thereafter. SWJs are prevalent in some neurological diseases such as progressive supranuclear palsy (PSP). However, they are also common in normal healthy subjects and in patients with Parkinson's disease (PD).

Patients with PSP and those with early stages of PD often appear to present similarly. It would be beneficial to be able to differentially diagnose one disease from the other in a non-invasive manner. The following disclosure provides one such differential diagnostic method.

SUMMARY

A method and apparatus are disclosed for detecting the eye movements of a patient to provide a differential diagnosis of progressive supranuclear palsy (PSP) from Parkinson's disease (PD) in that patient. The method includes the step of identifying a plurality of at least partially repetitive eye movements of a patient to be diagnosed with one or the other of PSP or PD that over time define square wave jerks within a sequence of eye movements. Each square wave jerk of the plurality of square wave jerks is defined by a first horizontal saccadic movement that moves the eye away from a fixation target that is followed by a corrective saccadic movement towards the target shortly thereafter. A vertical component associated with the plurality of square wave jerks is measured. The vertical component is compared with a predetermined threshold value, such as the mean of control data±1 standard deviation, and the presence of PSP or PD is identified based upon the comparison of the vertical component with the threshold value whereby a vertical component statistically different (mean±1 standard deviation) from that of a normal subject or that PD patients identifies the patient as having PSP, whereas a vertical component that is (a) not statistically different (mean±1 standard deviation) from that of normal healthy subjects or PD patients or (b) is statistically different (mean±1 standard deviation) from that of PSP patients, identifies the patient as having PD.

Also contemplated is another method for providing a differential diagnosis of progressive supranuclear palsy (PSP) from Parkinson's disease (PD) in that patient. Here, the method includes the step of identifying a plurality of at least partially repetitive eye movements of a patient to be diagnosed with one or the other of PSP or PD that over time define square wave jerks within a sequence of eye movements. Each square wave jerk of the plurality of square wave jerks is defined by a first horizontal saccadic movement that moves the eye away from a fixation target that is followed by a corrective saccadic movement towards the target shortly thereafter. The saccade rate [number of saccades per unit time, e.g., number per second (N/s)] is determined and that rate is compared with a predetermined threshold value, such as the mean of control data±1 standard deviation, and the presence of PSP or PD is identified based upon the comparison of the saccade rate with the threshold value whereby a saccade rate statistically different (mean±1 standard deviation) from that of normal subjects or from that PD patients identifies the patient as having PSP, whereas a saccade rate that is statistically different (mean±1 standard deviation) from that of normal subjects or PSP patients identifies the patient as having PD.

As used herein, the word "subject" with or without modifiers such as "healthy" and "normal" refers to a person free from apparent symptoms of PSP or PD, data from whom are used as control values.

BRIEF DESCRIPTION OF THE DRAWINGS

FIG. 7 in two panels, as FIG. 7A and FIG. 7B, provides two graphs that show saccade data from PSP patients (x), PD patients (○) and normal healthy subjects (Δ), and in which ovals surrounding the data points indicate the region of the mean±1 standard deviation.

DETAILED DESCRIPTION OF AN ILLUSTRATED EMBODIMENT

A process is described herein that automatically identifies SWJs in the eye movements of a person, during visual fixation of a small target. The results show that SWJs are common in both PSP patients and normal healthy subjects. Other results show that SWJs are also common in Parkinson's disease (PD) patients. However, several SWJ parameters (e.g., SWJ rates, magnitudes, percentage of small saccades that are part of SWJs, average inter-saccadic intervals for the SWJs, saccadic rates, saccadic peak velocities within SWJs, standard deviation of the direction difference between pairs of saccades in the SWJs, standard deviation of the difference between the horizontal and the direction of the saccades in the SWJs) have been found to be different in the PSP group.

The vertical components of SWJs of PD and healthy subjects are similar; i.e., not statistically significantly different (mean±1 standard deviation). On the other hand, the saccade rate between PD patients and normal healthy subjects is just different enough that the two can be distinguished. That is, the saccade rates of PD patients and normal healthy subjects are statistically significantly different (mean±1 standard deviation).

Thus, the objective characterization of SWJs can provide a powerful tool in the differential diagnosis of oculomotor diseases such as PSP and PD.

Although people spend about 80% of their waking lives fixating their gaze, the contribution of impaired fixational eye movements to vision loss has been overlooked as a potential clinical malady. This gap in knowledge has prevented the field from developing new treatments and diagnostics to ameliorate visual deficits due to impaired fixational eye movements.

In general, a healthy subject or a patient will fixate on a target while his/her eye movements are recorded with an eye tracking system. Any eye tracking system available can be used for this purpose: video tracking, scleral search coil, etc. The temporal and spatial resolution of the eye tracking systems is ideally high enough to allow the detection of small saccades during fixation. A sampling rate of 500 Hz or higher is recommended, although small saccades can nevertheless be detected with lower rates at the expense of non-optimal performance.

Figure 1:
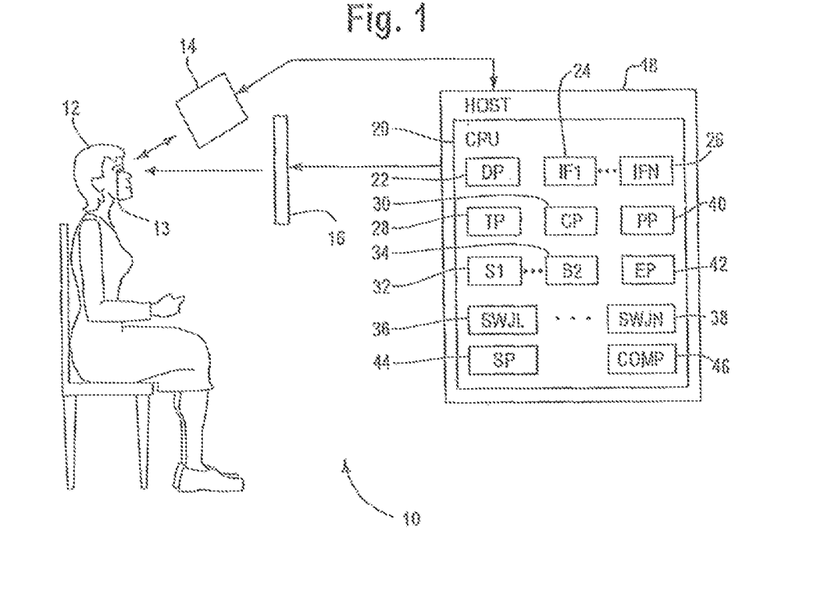
FIG. 1 is a block diagram of a system for detecting and characterizing square wave jerks in the eye movements of a subject to diagnose neurological disease, shown generally in accordance with an illustrated embodiment of the invention.
Figure 3:
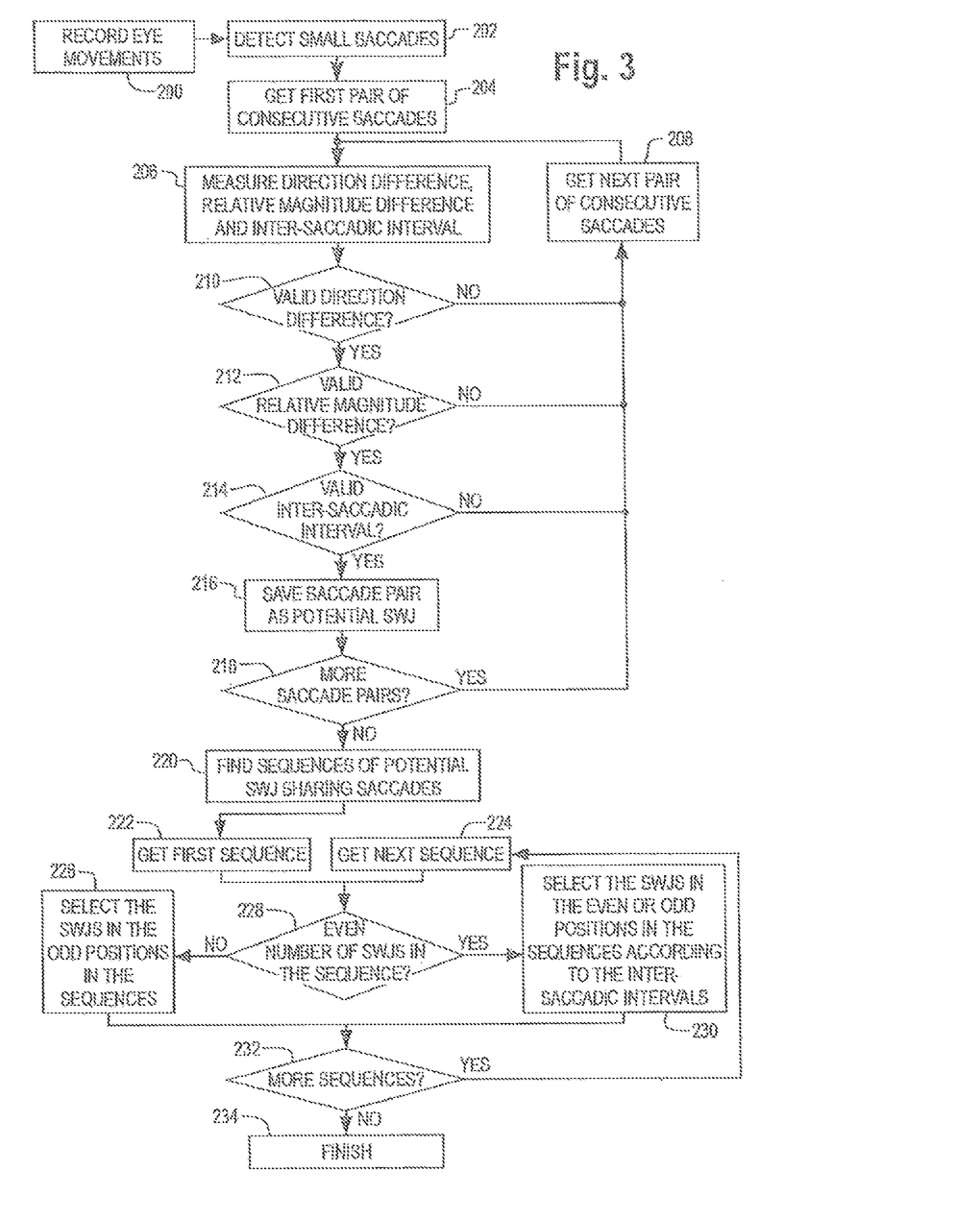
FIG. 3 is a flow chart of steps that may be followed by the system of FIG. 1.

FIG. 1 shows an example of an eye tracking system 10 for detecting eye movement under an illustrated embodiment of the invention. FIG. 3 is a flow chart of steps that can be followed by the system 10. Included within the system 10 can be an eye tracking device 14, such as the EyeLink II by SR Research (sr-research.com/fixed_tech_spec.php) or other equivalent eye tracking systems such as the IVIEW™ HI-SPEED 1250 tracking system by SensoMotoroic Instruments (smivision.com/en/eye-gaze-tracking-systems/products/iview-x-hi-speed.html).

Also included within the system 10 can be a display 16 and host 18. The host 18 includes a central processing unit (CPU) 20 embodied as hardware and a number of associated processors (described below), that can also be embodied as hardware. In this case, the processors can each be defined by a respective hardware processor executing one or more programs loaded from a non-transitory computer readable medium (memory).

The objective of the data collection of the system 10 is to automatically and objectively detect square wave jerks (SWJs) present in the eye movement trace. SWJs are characterized by one small horizontal saccade that moves the eye away from the fixation target, followed by a corrective saccade towards the target shortly thereafter.

Figure 2:
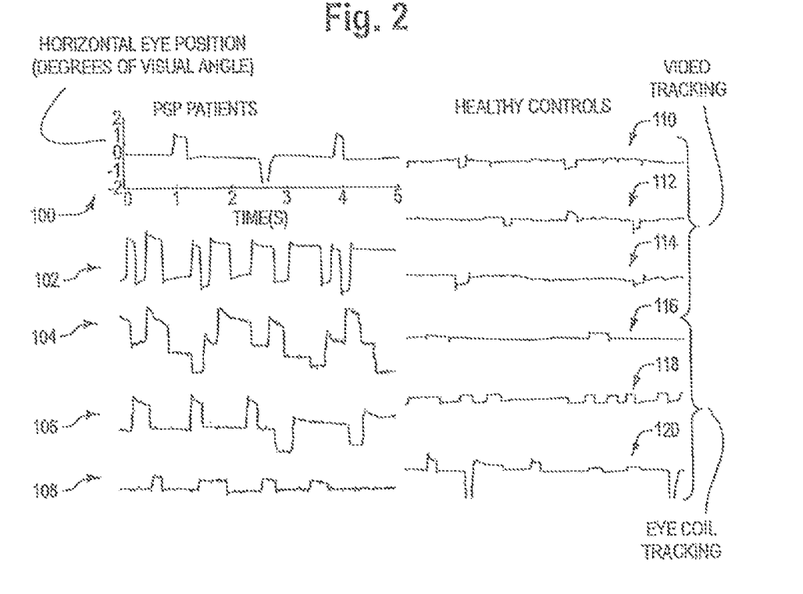
FIG. 2 is a number of graphs of saccades of patients and healthy subjects.

FIG. 2 provides examples of eye movement recordings for PSP patients and healthy subjects. A first graph 100 shows an example of horizontal eye position in degrees of visual angle versus time. Graphs 102, 104, 106, 108 provide other examples of eye position versus time for a group of PSP patients, whereas graphs 110, 112, 114, 116, 118 and 120 provide examples of eye position for healthy test subjects.

A display processor 22 within a controller 20 of the system 10 presents the fixation target to a subject 12 on the display 16. As the subject 12 fixates in the target on the display 16, the eye tracking device 14 detects and records 200 the position and movement of the eyes 13 of the subject 12. A tracking processor 28 within the host 18 can receive the position of the eyes 13 and store it for later transfer to a saccade processor 30.

The saccade processor 30 can receive the eye position measurements, can detect 202 substantially all the consecutive pairs of saccades (up to a certain maximum magnitude, for instance, 5 degrees). Any method to detect small saccades can be used by the saccade processor 30. Two main algorithms have been used in the literature: the Martinez-Conde and Macknik algorithm [Martinez-Conde, Macknik, Hubel (2000) *Nature Neuroscience* 3:251-258] and the Engbert algorithm [Engbert, Kliegl (2003) *Vision Res* 43:1035-1045].

The first step of the Martinez-Conde and Macknik process that can be used by the saccade processor 30 is the differentiation of the data (horizontal and vertical position), so that each element represents the instantaneous velocity of the eye in horizontal and vertical space, then data can then be smoothed with a 31 milliseconds (ms) wide unweighted boxcar filter to reduce noise. Then, the direction and size of the motion between each two samples is calculated. The size of the motion represents the velocity of movement in polar coordinates and the direction is differentiated to obtain the rate-of-turn indicator. The saccade processor 30 determines that the eye is moving when the polar velocity is more than 3° per second (s) and the rate-of-turn is smaller than 15°. Finally, only detected eye movements of more than 3 arc minutes (arcmin) and less than 2° are considered saccades.

Under the Engbert process, the saccade processor 30 can first transform the time series of eye positions into velocities in accordance with the equation $$\vec{v}_n = \frac{\vec{x}_{n+2} + \vec{x}_{n+1} - \vec{x}_{n-1} - \vec{x}_{n-2}}{6\Delta t},$$

that represents a moving average of velocities over 5 data samples in order to suppress noise. As a consequence of the random orientations of the velocity vectors during fixation, the resulting mean value of noise is effectively zero. A multiple of the standard deviation of the velocity distribution is used as the detection threshold. Detection thresholds are computed independently for horizontal and vertical components and separately for each trial, relative to the noise level.

Typical values for the threshold are 4, 5 or 6 times the standard deviation of the velocity. Therefore, the process used by the saccade processor 30 is robust with respect to different noise levels between different trials and subjects. Additionally, minimum saccade duration of 8 or 12 ms is required to further reduce noise. Finally, only binocular saccades are used, that is, saccades with at least 1 sample of overlap between the two eyes.

The principal advantage of the Engbert algorithm is that it adapts to the level of noise of the data. However, although this improves its performance in noisy situations it can produce non-optimal results in low noise conditions where the Martinez-Conde and Macknik algorithm behaves better.

As the saccades 32, 34 are identified (or after), a pairing processor 40 can determine and combine consecutive pairs of associated saccades 32, 34 into potential SWJs 36, 38. The pairing processor 40 can get a first pair of consecutive saccades 204 and measure a direction difference, a relative magnitude difference and an inter-saccade difference 206. The pairing processor 40 can use three criteria 210, 212, 214 to determine whether a pair of saccades 32, 34 is a SWJ 36, 38. If a pair of saccades 32, 34 does not meet each of the three criteria, then the pair can be discarded.

Figure 4A:
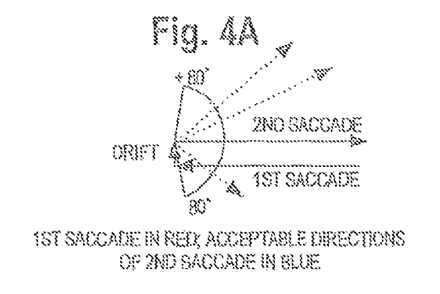
FIG. 4 graphically depicts steps in identifying square wave jerks that may be followed by the system of FIG. 1.

The First criterion requires that the two consecutive saccades 32, 34 should have (loosely) opposite directions. In a perfect SWJ this difference would be exactly 180°. Allowing for some variability, a pair of saccades meets this criterion 210 if the direction difference is in the range 180°±80°. (See FIGS. 4A and 4D).

Figure 4B:
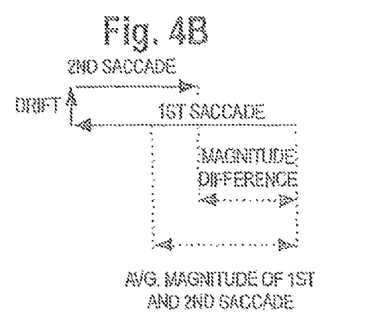
Figure 4C:
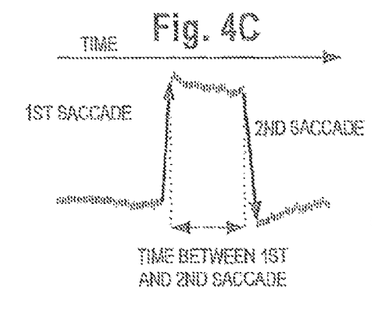
Figure 4D:
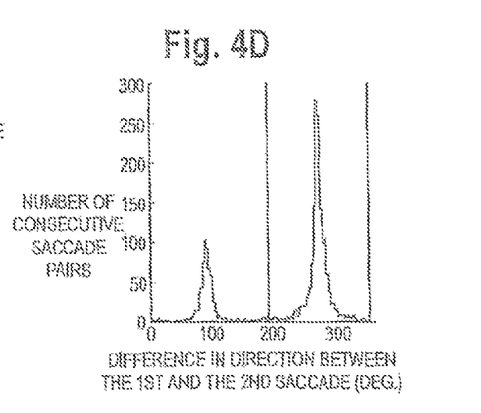
Figures 4E, 4F:
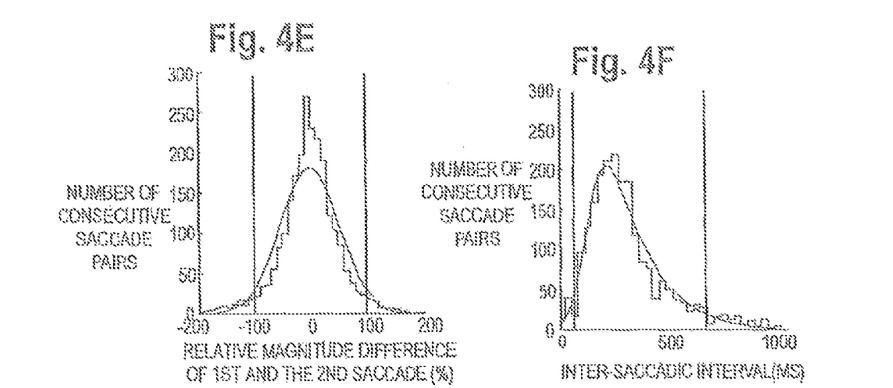
Figure 5A:
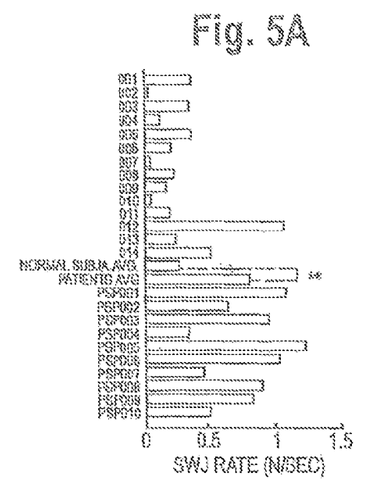
FIG. 5 compares statistics of patients and healthy subjects that can be provided by the system of FIG. 1.
Figure 5B:
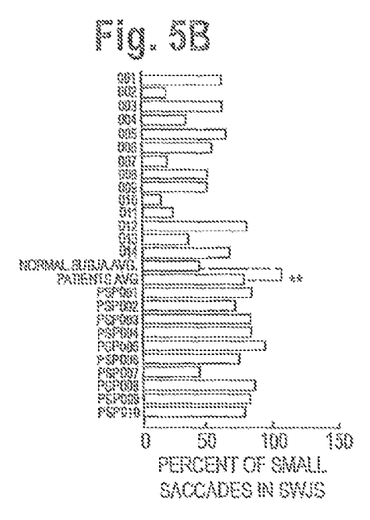
Figure 5C:
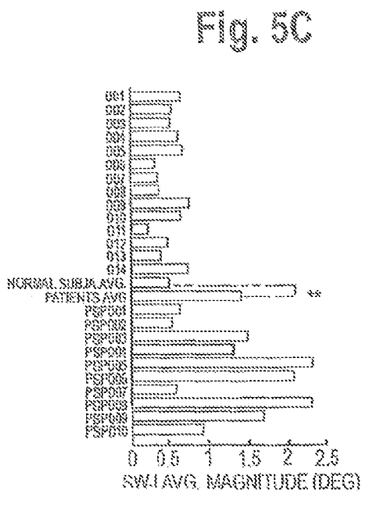
Figure 5D:
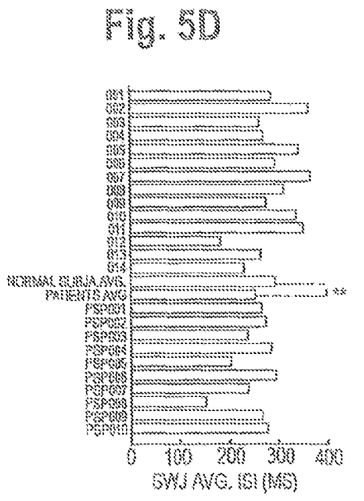
Figure 5E:
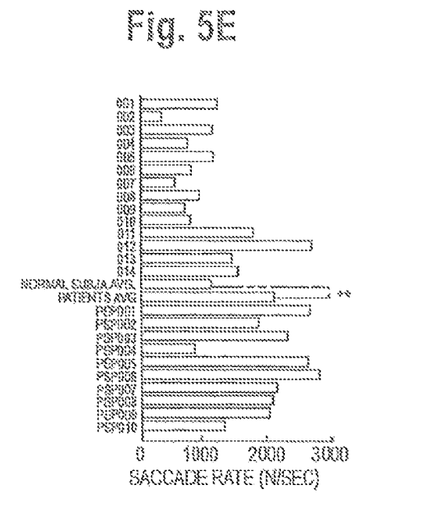
Figure 5F:
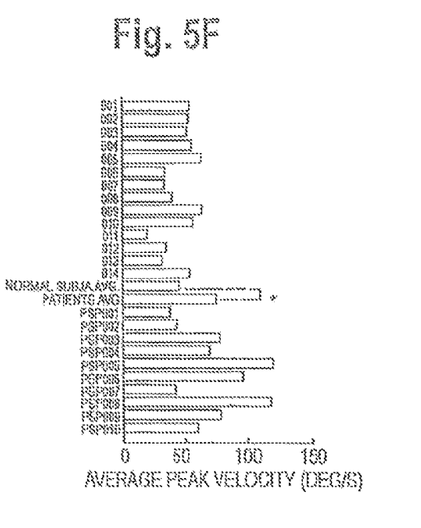
Figure 5G:
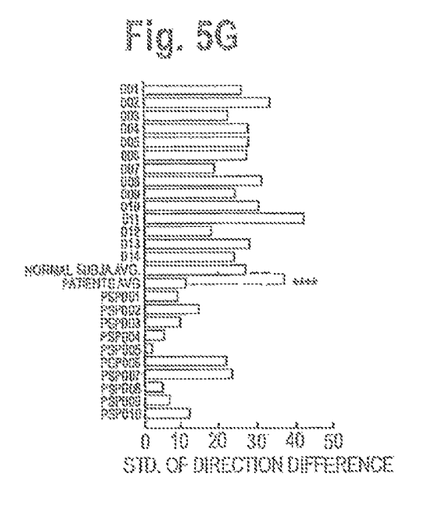
Figure 5H:
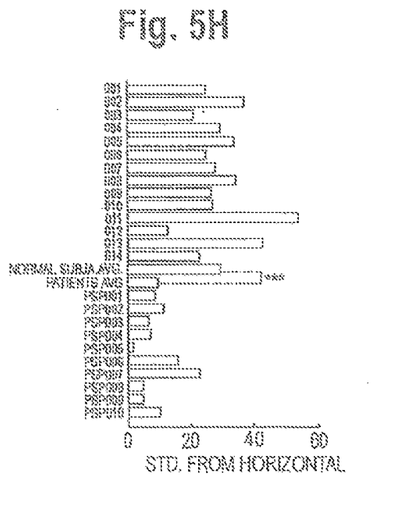

The second criterion 212 is that the two consecutive saccades 32, 34 should have similar magnitudes as shown in FIGS. 4B and 4E. A disimilarity index can be objectively calculated as the magnitude difference between the 1st and the 2nd saccade divided by the average magnitude of both saccades (expressed in percent terms) by the following equation, $$\frac{\text{magnitude of } 1^{st} \text{ saccade} - \text{magnitude of } 2^{nd} \text{ saccade}}{\text{average magnitude of } 1^{st} \text{ and } 2^{nd} \text{ saccade}} \times 100$$

An ideal SWJ (where the two saccades have equal magnitudes) would have an index of 0%. A pair of saccades is considered a SWJ if the index is in the range±100%.

The third criterion 214 can require that the two consecutive saccades should have Inter-Saccadic Interval (ISI) (between the end of the 1st saccade and the beginning of the 2nd saccade) in the range 70 ms-650 ms. (See FIGS. 4C and 4F).

Once the saccade processor 30 has processed a saccade pair, the processor 30 can determine if there are any more saccade pairs 218. If so, then the saccade processor 30 retrieves the next pair 208 of the sequence and the process repeats.

The specific numeric values for the three different criteria were optimized based on a data from a set of PSP patients (see FIGS. 4D, 4E, 4F). The system 10 can also be used with other criteria values where the other criteria values show a better performance.

As a last step, an elimination processor 42 can locate sequences of potential SWJs sharing saccades 220 and eliminate the SWJs 36, 38 that share saccades 32, 34. The result of the previous step is a sequence of pairs of saccades that meet the initially defined SWJ criteria. However, it is possible in some cases that these pairs are linked by a shared saccade. To solve this problem and have saccades that are only part of a unique SWJ, the following rule can be used: if the number of SWJs linked by shared saccades is odd, then the SWJs in even positions in the sequence of SWJs are discarded. That is one way to ensure that all the saccades are part of only one SWJ.

If the number is even, then it is impossible to achieve this result and at least one saccade will not be part of any SWJ. In this case the odd or even SWJs can be discarded depending upon which choice provides a shorter average inter-saccadic interval.

As such, the elimination processor 42 can retrieve a first sequence 222 of potential SWJs and determine the number of potential SWJs that share a saccade. If the number of SWJs with shared saccades is even 228, then the elimination processor 42 selects the SWJs in the even or odd positions in the sequence according to the inter-saccadic intervals 230. If not, then the elimination processor 42 selects the SWJs in the odd positions of the sequence 226. If there are any more sequences 232, the process repeats. If not, then the elimination process ends 234.

Following identification of SWJs 36, 38, that meet the appropriate criteria, the remaining SWJs 36, 38 can be transferred to a statistics processor 44. Within the statistics processor 44, the SWJs 36, 38 of PSP patients can be compared with healthy subjects. FIG. 5 provides SWJ parameter comparison between a population of healthy subjects and a population of PSP patients.

The system 10 can be used to automatically compute several SWJ parameters that can help to determine whether a person is healthy (a subject) or has certain neurological diseases. In all the panels of FIG. 5, the upper rows (labeled "001" through "014") correspond to respective healthy subjects and the lower rows (labeled "PSP001" through "PSP010") correspond to respective PSP patients. The horizontal bar (labeled "Normal subjs.avg.") is the average of the healthy subjects' population and the horizontal bar (labeled "Patients.avg.") is the average of the PSP patients' population respectively.

The parameters represented in each panel of FIG. 5 are (from left to right and top to bottom): (A) Number of SWJ per second; (B) Percentage of small saccades that are part of SWJs; (C) Average magnitude of the saccades that are part of SWJs; (D) Average inter-saccadic interval for the SWJs; (E) Number of saccades per second; (F) Average peak velocity of the saccades in SWJs; (G) Standard deviation of the direction difference and (H) Standard deviation of, the difference between the horizontal and the direction of the saccades in the SWJs. All the parameters (with the exception of the inter-saccadic interval) are significantly different between the two populations (two-tailed t-test).

Any of a number of the statistics of FIG. 5 can be the basis of a screening test for detecting PSP. For example, the standard deviation of direction difference in FIG. 5 (G) shows a greater than a two to one difference between the PSP patients and normal subjects. In this case, the standard deviation of direction difference of a subject 12 tested with the system 10 can be compared within a comparator 46 with the standard deviation of direction difference of a normal subjects to detect PSP. Other statistics of FIG. 5 can be used in a similar manner.

In another embodiment of the invention, differences in SWJ characteristics between normal patients (healthy subjects) and patients with Progressive Supranuclear Palsy (PSP) can also be used to identify patients with Parkinson's disease (PD). In their early stages, these two afflictions cannot be definitively or differentially diagnosed under previously known methods because their symptoms are so similar. It is critical nevertheless to differentiate between them as early as possible as their neurological bases and treatment regimens are quite different. It has been found that the characteristics of SWJs in these two diseases are different, and that the measurement of SWJ characteristics in these two patient populations therefore provide as a sensitive method to differentially diagnose these diseases earlier than other tests.

It is also believed that the measurement of SWJ characteristics similarly serve as a sensitive test for other neurological disorders as well. Examples include such afflictions as stroke, Friedrich's ataxia, cerebellar disease, multiple sclerosis, cerebral lesions, strabismus, and nystagmus.

It has been found that the method described herein accurately differentially diagnoses PSP from PD, in part, because PD patients are more like normal patients for the types of eye movements used in the diagnosis. This is a major advance because there is no previous method to accurately and non-invasively differentially diagnose PSP from PD.

PSP is a much more debilitating disease than PD, although at the early stages they appear similar. Because of the similar symptoms, patients with PSP are often misdiagnosed as having PD and are given L-DOPA or other PD drugs in levels appropriate for PD, but way too low for PSP patients. As a result, PSP patients misdiagnosed with PD typically suffer much more than they otherwise would, had they been accurately diagnosed. The method described below demonstrates that accurate diagnosis of PSP can be made from a simple non-invasive eye movement analysis.

In this regard, it has been found that PSP is distinguishable from Parkinson's disease because the vertical component of SWJ's is smaller for PSP patients than for Parkinson's patients. This effect exists between PSP patients and healthy people (subjects), as well.

Detection in this regard can include an eye movement processing apparatus (including one or more of device 14 and special purpose processors 20, 30, 40) that detects SWJs as discussed above. One or more programmed processors, such as those shown in FIG. 1 (e.g., processors 42, 44), can then analyze a vertical component of each of the SWJs.

In this regard, the vertical component can be manifested as a tilting of the horizontal saccades by a few degrees. As above, a standard deviation of directional difference can be determined in the vertical component for the deviation away from the fixation target versus the corrective saccade towards the target. This can be compared with a normal subject and/or with normal subjects as a basis for determining a set of threshold values for PSP and Parkinson's disease.

In addition, the number of vertical deviations per time period as well the magnitude of the vertical deviation can be collected. The velocity of the vertical deviation can be measured.

Figure 6:
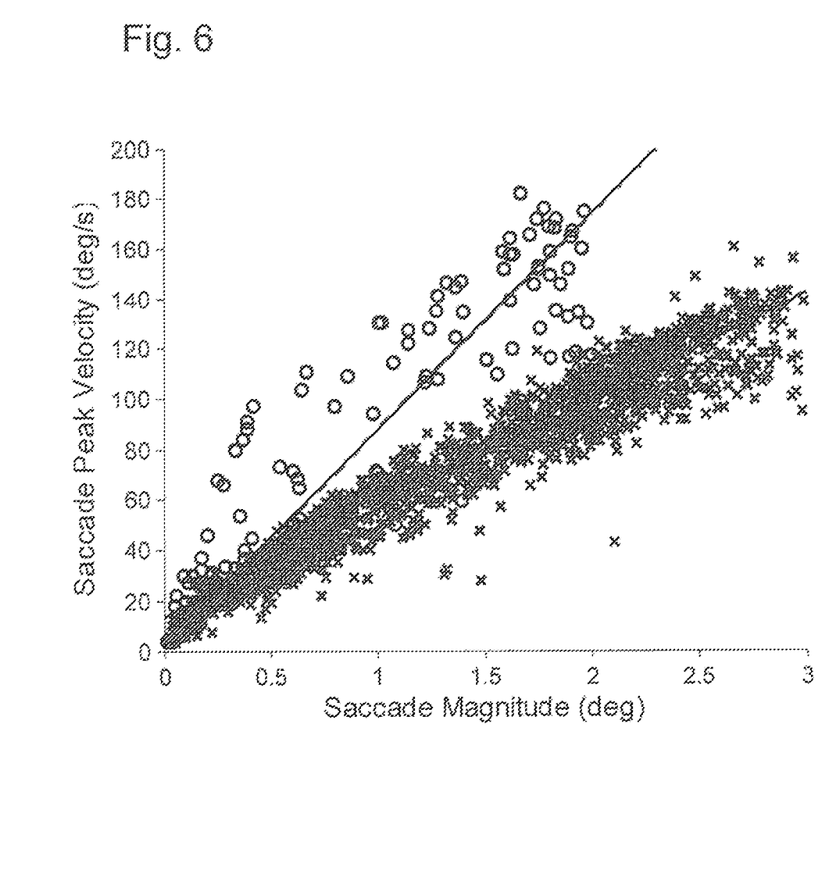
FIG. 6 is a graph of saccade magnitude (abscissa) versus saccade speed (ordinate) for PD patients (○) and PSP patients (x)

The data points of FIG. 6 illustrate individual saccades. It is seen the PD patients have faster saccades than PSP patients. These data provide the "main sequence slope" utilized in FIG. 7 in which saccade rate is plotted vs. main sequence slope in FIG. 7A and the normalized saccade vertical component is plotted vs. main sequence slope in FIG. 7B.

Figures 7, 7A:
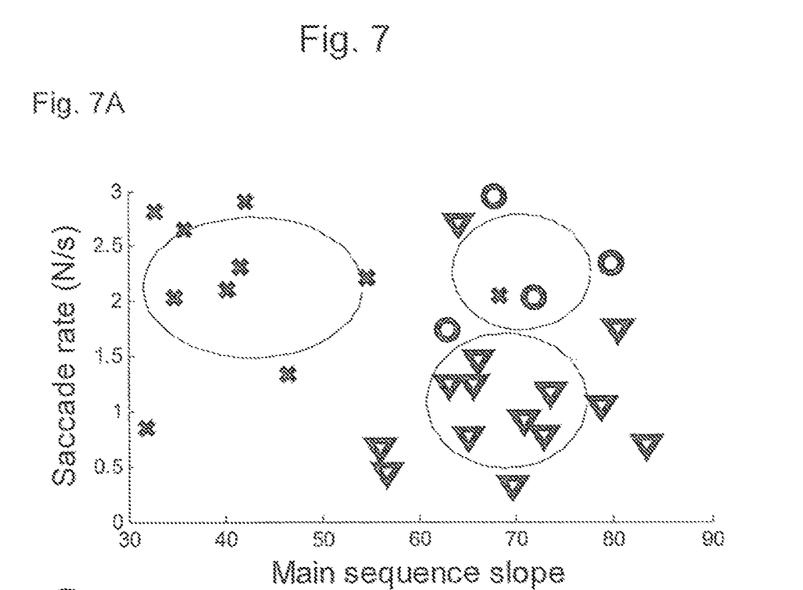
Figure 7B:
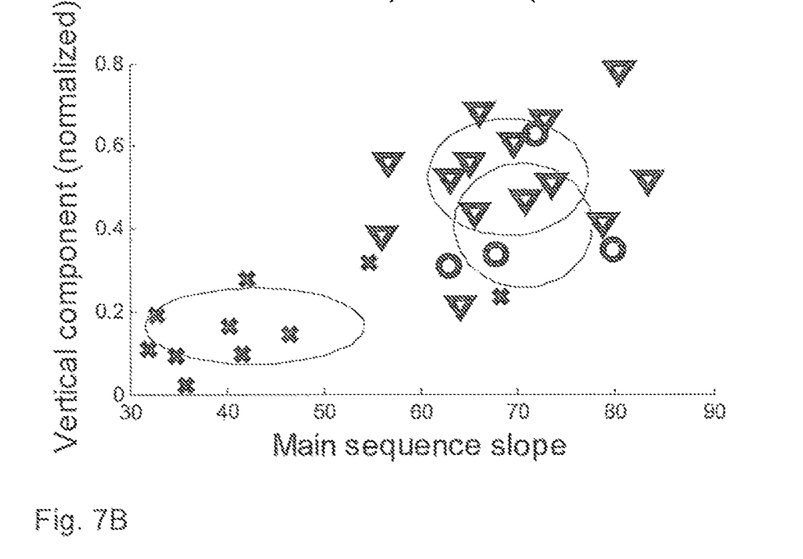

The data used in FIGS. 6 and 7 were subjected to statistical analysis. The significance testing statistics in the table below were calculated using ANOVA and corrected for multiple comparisons using Tukey's Honest Significant Difference. As is seen, differences between control (normal healthy) patients and PSP patients were highly significant, as were differences between PSP and PD patients for vertical component and main sequence slope, whereas there was little difference in saccade rate between PSP and PD patients. There were also not significant differences between control and PD patients in vertical component and main sequence slope.

| Multiple Comparisons Between Groups (adjusted p-values) | | | |
|---|---|---|---|
| | Vertical component | Main sequence slope | Saccade rate |
| Control-PSP | 0.0000025 | 0.0000022 | 0.0071293 |
| Control-PD | 0.4250289 | 0.9916481 | 0.0320478 |
| PSP-PD | 0.0233523 | 0.0002209 | 0.9880972 |

The algorithm used successfully characterized patients in each group (PSP, PD or control) based on three dynamical eye movement parameters in fixation saccades: vertical component, rate and velocity. PSP patients are distinguished from controls based on lack of vertical component, slower velocity or higher rate. PSP and PD patients are distinguished from each other because PSP patients have slower and more horizontal saccades. PD patients and controls (normal healthy subjects) can be distinguished because PDs have higher saccade rates.

The collected vertical data can be compared with that of PSP patients as well as that of normal subjects. A first set of threshold values can be used to identify patients with Parkinson's disease. In a similar manner, a second set of threshold values can be used to identify patients with PSP. Other threshold values can be used to identify patients with stroke, Friedrich's ataxia, cerebellar disease, multiple sclerosis, cerebral lesions, strabismus, and nystagmus.

A specific embodiment of method and apparatus for detecting and characterizing square wave jerks in the eye movements of a subject, which can provide a powerful tool in the differential diagnosis of oculomotor and neurological disease, has been described for the purpose of illustrating the manner in which the invention is made and used. The method disclosed herein has extended the previously filed method of application Ser. No. 12/740,008 to include the capability of distinguishing PSP patients and control subjects from each other as well as from and patients affected with Parkinson's Disease (PD).

It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein. The use of the article "a" or "an" is intended to include one or more.

The invention claimed is:

1. A method for providing a differential diagnosis of a patient with progressive supranuclear palsy (PSP) from a patient with Parkinson's disease (PD) that comprises the steps of:
 a) identifying in a patient to be diagnosed with one or the other of PSP or PD a plurality of at least partially repetitive eye movements that over time define square wave jerks within a sequence of eye movements, each square wave jerk of the plurality of square wave jerks being defined by a first horizontal saccadic movement that moves the eye away from a fixation target that is followed by a corrective saccadic movement towards the target shortly thereafter;
 b) measuring a vertical component associated with the plurality of square wave jerks;

c) comparing the vertical component with a threshold value for normal healthy subjects or other patients with PSP or other patients with PD;

d) identifying the presence of PSP or PD in the patient to be diagnosed based upon the comparison of the vertical component with the threshold value whereby a vertical component statistically different from the threshold value of normal subjects or PD patients identifies the patient to be diagnosed as having PSP, whereas a vertical component that is (a) not statistically different from the threshold value of normal subject or (b) is statistically different from the threshold value of PSP patients identifies the patient as having PD.

2. The method for providing a differential diagnosis as in claim 1 further comprising obtaining a sequence of saccadic movements.

3. The method for providing a differential diagnosis as in claim 2 further comprising identifying pairs of consecutive saccadic movements of the sequence.

4. The method for providing a differential diagnosis as in claim 3 further comprising determining whether each saccadic movement of each identified pair is opposite the direction of the other saccadic movement and, if not, then discarding the pair.

5. The method for providing a differential diagnosis as in claim 4 further comprising determining whether a magnitude of each saccadic movement of each identified pair is comparable and, if not, then discarding the pair.

6. The method for providing a differential diagnosis as in claim 5 further comprising determining whether the pair of saccadic movements of each identified pair are temporally related by a predetermined time period and, if not, then discarding the pair.

7. The method for providing a differential diagnosis as in claim 6 further comprising collecting any remaining pairs of saccadic movements as square wave jerks.

8. The method for providing a differential diagnosis as in claim 7 further comprising comparing a set of parameters of the square wave jerks in a potential patient against the corresponding parameters of a healthy population.

9. The method for providing a differential diagnosis as in claim 8 further comprising defining the opposite direction of the saccadic movements in the pairs as 180 degrees, plus or minus 80 degrees.

10. The method for providing a differential diagnosis as in claim 9 further comprising defining the magnitude of each saccadic movements in the pairs comparable as the dissimilarity index is in the range±100%.

11. A method for providing a differential diagnosis of a patient with progressive supranuclear palsy (PSP) from a patient with Parkinson's disease (PD) that comprises the steps of:

a) identifying in a patient to be diagnosed with one or the other of PSP or PD a plurality of at least partially repetitive eye movements that over time define square wave jerks within a sequence of eye movements, each square wave jerk of the plurality of square wave jerks being defined by a first horizontal saccadic movement that moves the eye away from a fixation target that is followed by a corrective saccadic movement towards the target shortly thereafter;

b) determining the saccade rate of the patient;

c) comparing the saccade rate with a threshold value for normal healthy subjects or other patients with PD;

d) identifying the presence of PSP or PD in the patient to be diagnosed based upon the comparison of the saccade rate with the threshold value whereby a saccade rate statistically different from the threshold value of normal subjects or PD patients identifies the patient to be diagnosed as having PSP, whereas a saccade rate that is statistically different from the threshold value of normal subjects or PSP patients identifies the patient as having PD.

12. The method for providing a differential diagnosis as in claim 11 further comprising obtaining a sequence of saccadic movements.

13. The method for providing a differential diagnosis as in claim 12 further comprising identifying pairs of consecutive saccadic movements of the sequence.

14. The method for providing a differential diagnosis as in claim 13 further comprising determining whether each saccadic movement of each identified pair is opposite the direction of the other saccadic movement and, if not, then discarding the pair.

15. The method for providing a differential diagnosis as in claim 14 further comprising determining whether a magnitude of each saccadic movement of each identified pair is comparable and, if not, then discarding the pair.

16. The method for providing a differential diagnosis as in claim 15 further comprising determining whether the pair of saccadic movements of each identified pair are temporally related by a predetermined time period and, if not, then discarding the pair.

17. The method for providing a differential diagnosis as in claim 16 further comprising collecting any remaining pairs of saccadic movements as square wave jerks.

18. The method for providing a differential diagnosis as in claim 17 further comprising comparing a set of parameters of the square wave jerks in a potential patient against the corresponding parameters of a healthy population.

19. The method for providing a differential diagnosis as in claim 18 further comprising defining the opposite direction of the saccadic movements in the pairs as 180 degrees, plus or minus 80 degrees.

20. The method for providing a differential diagnosis as in claim 19 further comprising defining the magnitude of each saccadic movements in the pairs comparable as the dissimilarity index is in the range±100%.

21. An apparatus that detects and characterizes eye movements of a subject, for the differential diagnosis of a patient with progressive supranuclear palsy (PSP) from a patient with Parkinson's disease (PD) comprising:

a processor that processes a sequence of repetitive, involuntary eye movements, each of the plurality of involuntary eye movements defined by a first horizontal saccadic movement that moves the eye away from a fixation target followed by a corrective saccadic movement towards the target shortly thereafter;

a processor that measures vertical components associated with the plurality of repetitive eye movements;

a processor that compares the vertical components with a threshold value; and a processor that differentially identifies progressive supranuclear palsy from Parkinson's disease based upon the comparison of the vertical component with the threshold value.

22. The apparatus for the differential diagnosis of a patient with progressive supranuclear palsy (PSP) from a patient with Parkinson's disease (PD) as in claim 21, wherein the eye movements identified by the processor further comprises a sequence of saccadic movements.

23. The apparatus for the differential diagnosis of a patient with progressive supranuclear palsy (PSP) from a patient with Parkinson's disease (PD) as in claim 22 wherein the eye movements identified by the processor further comprises pairs of consecutive saccadic movements of the sequence.

24. The apparatus that detects and characterizes eye movements as in claim 23, wherein the processor that identifies eye movements determines whether each saccadic movement of each identified pair is opposite the direction of the other saccadic movement and, if not, then discards the pair.

25. The apparatus that detects and characterizes eye movements as in claim 24, wherein the processor that identifies eye movements determines whether a magnitude of each saccadic movement of each identified pair is comparable and, if not, then discards the pair.

26. The apparatus that detects and characterizes eye movements as in claim 25, wherein the processor that identifies eye movements determines whether the pair of saccadic movements of each identified pair are temporally related by a predetermined time period and, if not, then discarding the pair.

27. The apparatus that detects and characterizes eye movements as in claim 26, wherein the processor that identifies eye movements collects any remaining pairs of saccadic movements as square wave jerks.

28. The apparatus that detects and characterizes eye movements as in claim 27, wherein the processor that identifies eye movements compares a set of parameters of the eye movements in a potential patient against the corresponding parameters of a healthy population.

29. The apparatus that detects and characterizes eye movements as in claim 28, wherein the processor that identifies eye movements defines the opposite direction of the saccadic movements in the pairs as 180 degrees, plus or minus 80 degrees.

30. A system that detects and characterizes eye movements of a patient, for the differential diagnosis of a patient with progressive supranuclear palsy (PSP) from a patient with Parkinson's disease (PD) comprising:

- eye movement processing apparatus that identifies a plurality of square wave jerks within a sequence of repetitive eye movements, each of the plurality of square wave jerks defined by a first horizontal saccadic movement that moves the eye away from a fixation target followed by a corrective saccadic movement towards the target shortly thereafter;
- a processor that measures vertical components associated with the plurality of square wave jerks;
- a processor that compares the vertical components with a threshold value or the saccade rate; and
- a processor that identifies PSP or PD based upon the comparison of the vertical component with the threshold value.

* * * * *